US009895388B1

(12) United States Patent
Mettert et al.

(10) Patent No.: US 9,895,388 B1
(45) Date of Patent: Feb. 20, 2018

(54) METHODS AND COMPOSITIONS USEFUL FOR CONTROLLING CUTANEOUS MITES

(71) Applicant: ParaPRO, Carmel, IN (US)

(72) Inventors: Kerry W. Mettert, Westfield, IN (US); William H. Culpepper, Carmel, IN (US)

(73) Assignee: ParaPRO, Carmel, IN (US)

( * ) Notice: Subject to any disclaimer, the term of this patent is extended or adjusted under 35 U.S.C. 154(b) by 122 days.

(21) Appl. No.: 13/951,835

(22) Filed: Jul. 26, 2013

Related U.S. Application Data

(60) Provisional application No. 61/676,644, filed on Jul. 27, 2012.

(51) Int. Cl.
*A61K 31/7048* (2006.01)

(52) U.S. Cl.
CPC ................................ *A61K 31/7048* (2013.01)

(58) Field of Classification Search
None
See application file for complete search history.

(56) References Cited

U.S. PATENT DOCUMENTS

| | | | | |
|---|---|---|---|---|
| 4,150,141 | A | 4/1979 | Berger | |
| 4,464,390 | A | 8/1984 | Kochansky et al. | |
| 5,496,931 | A * | 3/1996 | Boeck | C07H 17/08 424/405 |
| 6,063,771 | A | 5/2000 | Snyder | |
| 6,342,482 | B1 | 1/2002 | Snyder | |
| 6,933,318 | B1 | 8/2005 | Kassebaum et al. | |
| 7,030,095 | B2 * | 4/2006 | Janssen | A01N 25/02 424/405 |
| 7,612,100 | B2 | 11/2009 | Koyanagi et al. | |
| 2002/0035070 | A1 | 3/2002 | Gardlik et al. | |
| 2002/0164381 | A1 | 11/2002 | Shacknai et al. | |
| 2003/0026822 | A1 * | 2/2003 | Janssen et al. | 424/405 |
| 2006/0121073 | A1 * | 6/2006 | Goyal | A01N 25/04 424/405 |
| 2008/0299220 | A1 | 12/2008 | Tamarkin et al. | |
| 2009/0105276 | A1 | 4/2009 | Tambi | |

FOREIGN PATENT DOCUMENTS

| | | | | |
|---|---|---|---|---|
| EP | 0375316 | A1 * | 6/1990 | C07H 17/08 |
| EP | 2248422 | A1 * | 11/2010 | A01N 43/22 |

OTHER PUBLICATIONS http://en.wikipedia.org/wiki/Ivermectin.
http://en.wikipedia.org/wiki/Permethrin.
http://en.wikipedia.org/wiki/Scabies.
http://www.okapiland.com/arthropod/?s=0&n=Sarcoptiformes.
Meinking, B.A., Terri L. et al., The Treatment of Scabies With Ivermectin, The New England Journal of Medicine, pp. 26-30, Jul. 6, 1995.

* cited by examiner

*Primary Examiner* — Layla D Berry
(74) *Attorney, Agent, or Firm* — Woodard, Emhardt, Moriarty, McNett & Henry, LLP

(57) ABSTRACT

The present invention relates to compositions and methods useful for the topical treatment of cutaneous mites comprising spinosyn or a physiologically acceptable derivative or salt thereof.

30 Claims, 1 Drawing Sheet

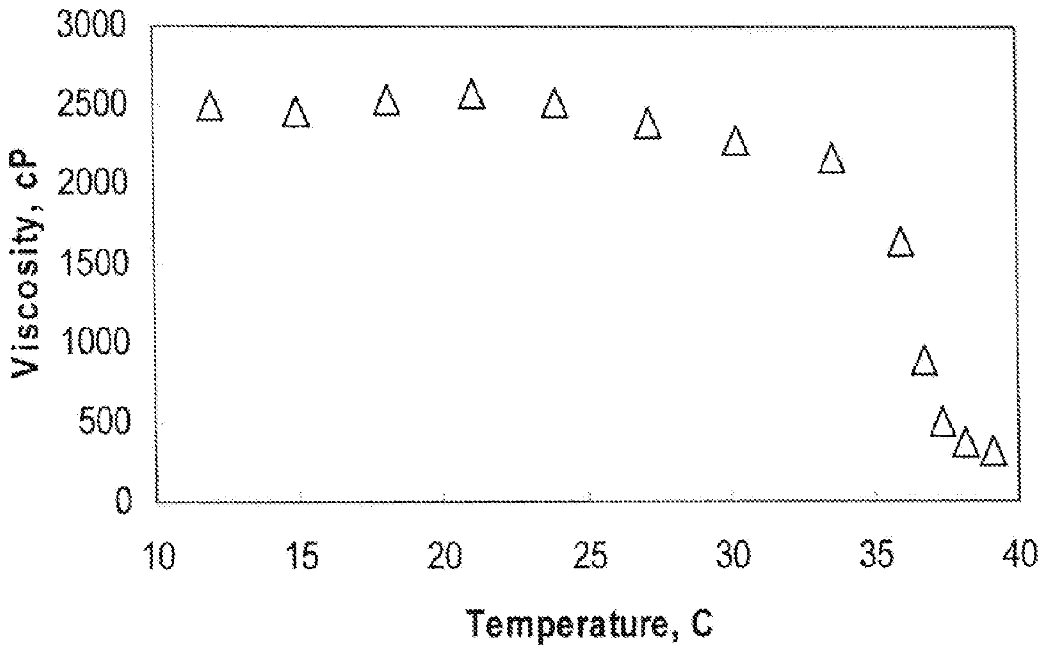
3000
2500
2000
1500
1000
500
0
Viscosity, cP
10
15
20
25
30
35
40
Temperature, C

METHODS AND COMPOSITIONS USEFUL FOR CONTROLLING CUTANEOUS MITES

REFERENCE TO RELATED APPLICATION

This application claims the benefit of priority from U.S. Provisional Patent Application Ser. No. 61/676,644, filed Jul. 27, 2012, which is hereby incorporated by reference in its entirety.

BACKGROUND

Aspects of the present invention pertain to the treatment of parasites on humans and/or animals using externally-applied agents. In certain of its embodiments, the present invention relates to methods and compositions that can be used in the prevention or control of mite infestations of the skin.

Parasitic infestations of the skin and/or hair are responsible for a number of conditions or disorders in both humans and animals. As an example, scabies is a contagious skin infection occurring in humans and animals. In humans, the disease is caused by the parasitic mite *Sarcoptes scabiei* which burrows under the host's skin causing allergic itching which is usually worse at night. The cutaneous diagnostic signs include multiple papules, minute vesicles and occasional linear tracts. The disease is most frequently transmitted by skin-to-skin contact, and is associated with close personal contact. No age or socioeconomic class escapes the disease.

Complications of scabies include bacterial superinfection, sepsis, glomerulonephritis and progression to Norwegian or crusted scabies—a more severe, life-threatening form of the disease. In animals, the disease is commonly known as sarcoptic mange which is caused by other mites in the order Sarcoptiformes.

Current treatments of scabies in humans include the topical application of permethrin for most cases and the oral administration of ivermectin in more severe cases including cases where the patient suffers from an immune system disease, e.g., HIV/AIDS. Other treatments include the use of crotamiton and lindane.

The spinosyns are a family of macrolides produced by the fermentation of *Saccharopolyspora spinosa*. The spinosyns are commonly used as insecticides in agricultural settings and are used for the treatment of lice in humans. More recently, the spinosyns have been used to treat lice and their eggs.

Each spinosyn compound has a 12-membered macrocylic ring that is part of a tetracyclic ring system to which two different sugars are attached, the amino-sugar forosamine and the neutral sugar 2N,3N,4N-tri-O-methylrhamnose. Spinosyn A was the first spinosyn isolated from the fermentation broth of *S. spinosa*. However, subsequent studies have identified a number related derivatives that have been labeled A to J.

Needs exist for improved and/or alternative methods and compositions that are useful for controlling mites and other parasites in humans and animals. Aspects of the present invention are addressed to these needs.

SUMMARY

In certain aspects, the present invention relates to methods and compositions for treating a skin infection of mites. In one embodiment, the invention provides a method for controlling mites in a human, for example the parasitic mite

*Sarcoptes scabiei*, that includes topically applying to skin of the human a composition comprising:

(a) a mixture of spinosyns including 70% to 90% by weight Spinosyn A, 12% to 20% by weight Spinosyn D, and 2% to 15% by weight of at least three other, and optionally all, spinosyns selected from the group consisting of Spinosyn B, Spinosyn C, Spinosyn D, Spinosyn E, Spinosyn F, Spinosyn G, Spinosyn H, Spinosyn J, and Spinosyn K;

(b) one or more solubulizers for the mixture of spinosyns, said one or more solubilizers including benzyl alcohol;

(c) one or more stabilizers;

(d) one or more humectants;

(e) one or more emulsifying agents; and (f) one or more surfactant agents.

In another embodiment, the invention provides a composition for controlling mites of the order Sarcoptiformes, for example the parasitic mite *Sarcoptes scabiei*, that includes an effective amount of one or more spinosyns. The composition can also include one or more solubulizers; one or more stabilizers; one or more humectants; one or more emulsifying agents; and one or more surfactant agents.

In a further embodiment, the invention provides a method for controlling mites of the order Sarcoptiformes, for example the parasitic mite *Sarcoptes scabiei*, comprising topically applying to skin of a human or animal a composition comprised of an effective amount of one or more spinosyns.

In methods or compositions described above or elsewhere herein, in preferred aspects, one of, or a combination of two or more of, or all of, the following features also characterizes the composition:

(i) the composition is effective to penetrate to the stratum corneum of skin of a human or animal when applied externally to the skin;

(ii) the composition, when applied externally to the skin of the human or animal, does not require the presence of the spinosyn(s) in the systemic bloodstream of the human or animal for efficacy;

(iii) the composition, when applied externally to the skin of the human or animal, does not result in the presence of the spinosyn(s) in the systemic bloodstream of the human or animal;

(iv) the composition exhibits a decrease in viscosity of at least about 1000 cP when warmed from 20° C. to about 37° C.;

(v) the composition has a viscosity greater than 2000 cP at 20° C. and a viscosity less than 1000 cP at 37° C.; and (vi) the composition exhibits a nonlinear decrease in viscosity over at least one temperature range between 30° C. and 37° C.

Additional summaries are provided in the claims appended hereto, each of which considered a summary of an embodiment of the present invention.

The foregoing and still further aspects of the invention will become more apparent from the following detailed description and accompanying drawings.

BRIEF DESCRIPTION OF THE FIGURES

FIG. 1 shows the decrease in viscosity of one embodiment of the present invention as a function of temperature.

DETAILED DESCRIPTION

For the purposes of promoting an understanding of the principles of the invention, reference will be made to certain embodiments thereof and specific language will be used to describe the same. It will nevertheless be understood that no limitation of the scope of the invention is thereby intended, and alteration and modifications in the referenced embodiments, and further applications of the principles of the inventions as illustrated herein are contemplated as would normally occur to one skilled in the art to which the invention relates.

Unless otherwise indicated, all percentages and ratios used herein are by weight of the total composition.

The following words and phrases as used herein have the meanings set forth below.

The term "antioxidant" as used herein means any chemical compound that reduces the tendency of another chemical compound to deteriorate by inhibiting oxidation.

The term "controlling," "treatment," or "treating" as used herein refers to curative measures taken with respect to an infected patient as well as the prophylactic application to prevent the onset of an infection in a patient.

The term "spinosyns" and "spinosyn or a physiologically acceptable derivative thereof" as used herein refers to an individual spinosyn factor (A, B, C, D, E, F, G, H, J, K, L, M, N, O, P, Q, R, S, T, U, V, W, or Y), an N-demethyl derivative of an individual spinosyn factor, a salt of an individual spinosyn factor, or a combination thereof.

The term "effective agent" as used herein refers to spinosyn or a physiologically acceptable derivative thereof used to decrease the number of mites and/or mite eggs.

The term "effective amount" as used herein refers to an amount of spinosyn or physiologically acceptable derivative thereof sufficient to decrease the number of live mites and/or mite eggs. Illustratively, the effective amount can range from greater than about 0% to 10% by weight, preferably about 0.5 to about 5% by weight.

The term "effective time" as used herein refers to an amount of time sufficient to decrease the number of live mites and/or mite eggs. In one embodiment, the effective time can range from about one minute to about twenty-four hours, preferably from about 2 hours to about 12 hours.

The term "humectant" as used herein refers to one or more compounds that prevent the skin from losing moisture. Examples of humectants include, but are not limited to, glycerin, glucose, honey, lactic acid, polyethylene glycol, propylene glycol, sorbitol, sucrose, trehalose, esters, fatty alcohols and acids, polyols, hydrocarbons, non-volatile silicones, waxes, animal fats, vegetable oils, and mixtures thereof. Examples of esters useful herein include, but are not limited to diisopropyl sebacate, diisopropyl adipate, isopropyl myristate, isopropyl palmitate, myristyl propionate, ethylene glycol disterate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate and mixtures thereof.

The term "solubulizer" as used herein refers to solvents capable of solubilizing the effective agent. Examples of solubulizers include, but are not limited to, benzyl alcohol, isopropyl alcohol, ethyl alcohol, and methyl alcohol.

The term "solvents" as used herein includes other vehicle ingredients. Generally, solvents suitable for use in the compositions herein are either water or selected to be miscible with water and innocuous to the skin. Solvents suitable for use herein include, but are not limited to, water, $C_1$ to $C_{20}$ mono- or poly-hydric alcohols and their ethers, ethylene glycol monoethyl ether, glycerin, methylene chloride, diethylene glycol monobutyl ether, diethylene glycol monoethyl ether, diethylene glycol monoethyl ether, dimethyl sulphoxide, dimethyl formamide, tetrahydrofuran, propylene glycol, and mixtures thereof.

The term "stabilizer" as used herein includes other vehicle ingredients to prevent physical separation of the formulation. Stabilizers suitable for use herein include, but are not limited to, acrylates/aminoacrylates $C_{10}$-$C_{30}$ Alkyl PEG-20 Itaconate copolymer, long chain acyl derivatives (including but not limited to ethylene glycol distearate and ethylene glycol monostearate), alkanoamides (including but not limited to cocamide MEA), esters of long chain fatty acids (including but not limited to stearyl stearate), alkyl dimethylamine oxides, methylcellulose, hydroxybutyl methylcellulose, hydroxypropylcellulose, hydroxypropyl methylcellulose, hydroxyethyl cellulose, distearyl phthalic amid, di(hydrogenated) tallow phthalic amide, primary amines with a fatty alkyl moiety of at least 16 carbons, polyacrylic acids, polysaccharide gums, colloidal clays, and colloidal silica.

The term "vehicle" as used herein can comprise a solid, semi-solid, or liquid cosmetically or physiologically acceptable vehicle, to enable the effective agent to be conveyed to the skin at an appropriate concentration. The vehicle can itself be inert or it can possess cosmetic or pharmaceutical benefits of its own. When the vehicle is to be applied topically, such vehicles will act as dilutants, dispersants, or solvents for the effective agent, which therefore ensure that they can be applied to and be distributed evenly. The vehicle will preferably be one which can aid penetration of the effective agent into the skin to reach mites located in the stratum corneum. Vehicles suitable for use herein alone or in combination include, but are not limited to, solvents, thickeners, powders, fillers, plasticizers, lubricants, emollients, surfactants, antioxidants, emulsifying agents, stabilizers, and humectants.

The invention, in certain of its aspects, provides for the use of one or more spinosyns or physiologically acceptable derivatives or salts thereof for the manufacture of a medication that is useful for treating mite infections.

The invention also provides methods for treating a mite infection comprising topically administering a formulation comprising a spinosyn or a physiologically acceptable derivative or salt thereof, and a physiologically acceptable vehicle.

The invention also provides formulations for treating a mite infection comprising as an active ingredient a spinosyn, or a physiologically acceptable derivative or salt thereof, and a physiologically acceptable vehicle wherein the formulation is in the form of a topical cream. A particular benefit of this cream is the decrease in viscosity when applied topically which allows for easier and more uniform topical application of the active pharmaceutical ingredient. As is known, cream formulations may for example include suspensions or lotions.

The invention also provides for an article of manufacture comprising packaging and contained within said packaging, a formulation for treating a mite infection comprising a spinosyn or a physiologically acceptable derivative or salt thereof, and a physiologically acceptable vehicle.

Many factors play an important role when creating a formulation for consumer and pharmaceutical products. Such factors include, but are not limited to, cost, stability of the formulation, stability of the effective agent in the formulation, solubility of the effective agent in the formulation, solubilization of the effective agent in the formulation, rheological properties, color, and smell of the formulation. It is often difficult to predict how one additive to a formulation will affect these factors in the complex modern formulations of consumer and pharmaceutical products.

Composition of and for use in methods of the invention include one or more spinosyns or physiologically acceptable derivatives or salts thereof. Such compositions will typically include a mixture of spinosyn compounds, preferably including at least Spinosyn A and Spinosyn D, more preferably a mixture including Spinosyn A, Spinosyn B, and at least three other spinosyn compounds; such other spinosyn compounds can be selected from Spinosyn B, Spinosyn C, Spinosyn D, Spinosyn E, Spinosyn F, Spinosyn G, Spinosyn H, Spinosyn J, and Spinosyn K. In certain embodiments, all such other spinosyn compounds are included in the mixture along with Spinosyn A and Spinosyn B. These mixtures can be prepared by fermenting the organism *Saccharopolyspora spinosa* and recovering the mixture from the fermentation using known techniques. The mixture will typically include Spinosyn A in an amount greater than any other, for example in the range of 70% to 90% by weight of all spinosyns. Spinosyn D can be included in an amount of about 12% to about 20% by weight of all spinosyns. The remainder of the spinosyns, when present, can constitute about 2% to about 15% by weight of all spinosyns.

In addition to the one or more spinosyn compounds, compositions of and for use in methods of the present invention will desirably also include:

one or more solubulizers for the mixture of spinosyns, preferably including benzyl alcohol;

one or more stabilizers, preferably including hydroxyethyl cellulose;

one or more humectants, preferably including propylene glycol;

one or more emulsifying agents, preferably including Ceteareth-20 (the polyethylene glycol (PEG-20) ether of cetearyl alcohol), Steareth-20 (a synthetic polymer composed of polyethylene glycol and stearyl alcohol), and/or sorbitan monoesters; and/or one or more surfactant agents, preferably including stearalkonium chloride.

The formulated compositions of and for use in the invention can be prepared in any suitable manner. Typically, the ingredients are mixed to form a homogenous composition. Any suitable order of addition of the ingredients can be used, and heating can be used to facilitate mixing.

In one specific embodiment, the composition is constituted of the ingredients, and amounts, specified in Table 1:

TABLE 1

| Trade Name | INCI Name | Percent by Weight |
|---|---|---|
| | Deionized Water | 44 |
| Isopropyl Alcohol | Isopropyl Alcohol | 20 |
| Benzyl Alcohol | Benzyl Alcohol | 10 |
| Hexylene Glycol | Hexylene Glycol | 6 |
| Ammonyx4 | Stearalkonium chloride | 4.2 |
| Cetostearyl Alcohol NF | Cetearyl alcohol | 3 |
| Propylene Glycol | Propylene Glycol | 3 |
| Natrosol HX PHARM | Hydroxyethyl cellulose | 1.1 |
| Spinosyns* | Spinosyns | 1 |
| Procol-CS-20 | Ceteareth-20 | 0.9 |
| Butylated hydroxytolune | BHT | 0.1 |
| Sodium Hydroxide | Sodium Hydroxide | |
| Hydrochloric Acid | Hydrochloric Acid | |
| FD&C Yellow No. 6 granular powder | FD&C Yellow #6 | |

*Spinosyns were provided as a fermentation-produced product containing Spinosyn A (about 70-90%), Spinosyn D (about 12-20%), and also amounts of Spinosyns B, C, D, E, F, G, H, J, and K.

In one typical preparation, the composition defined in Table 1 is prepared by adding ingredients into a large jacketed stainless steel mixing vessel. This can begin with the addition of a portion of the deionized water (about 94% of the total water used) to the tank, followed by propylene glycol and then hydroxyethylcellulose, with mixing. With continued mixing, the tank contents are heated to 55-65° C. by circulating heated water in the tank jacket. Ceteareth-20 is added and the tank contents thoroughly mixed, after which stearalkonium chloride (Ammonyx4) is added and the contents again mixed. Cetearyl alcohol is added with continued mixing, after which hexylene glycol is added and the contents again mixed. A separately prepared solution of a portion of the benzyl alcohol and BHT is added to the tank, after which the remaining portion of the benzyl alcohol is added to the tank followed by mixing. Isopropyl alcohol is then added, with additional mixing, after which the spinosyns mixture is added and the tank contents mixed. A separately prepared solution of purified water and FD&C Yellow #6 is then added to the tank and the tank contents mixed. The pH of the contents is checked and if needed 1N hydrochloric acid is added to adjust the pH to 5.5 and 6.0. The remainder of the deionized water is then added to the tank, and the contents thoroughly mixed. The specific gravity of a sample of the tank contents is checked. If the specific gravity is between 0.930 and 0.980 g/mL at 25° C., deaeration is not necessary; otherwise, de-aeration can be performed with a vacuum pump at 60-80 cm Hg until the specific gravity of the composition is between 0.930 and 0.980 g/mL at 25° C.

When the preparative steps noted above are complete, cold water is circulated through the outer jacket of the tank to cool the product. At room temperature, cetostearyl alcohol forms small suspended crystals providing the composition with a creamy lotion-like appearance.

In certain modes of practicing the invention, the rheological properties of the formulated composition, for example the composition defined in Table 1, are controlled to provide particularly beneficial features in use. In illustrative forms, the formulated composition experiences a large drop in viscosity, e.g. at least about 1000 cP, when warmed from a temperature of 20° C. to 37° C. Desirably, the composition has a viscosity greater than 2000 cP at 20° C. and a viscosity less than 1000 cP at 37° C. Further, the composition can exhibit a nonlinear decrease in viscosity over at least one temperature range between about 30° C. and about 37° C. This decrease in viscosity can be facilitated by the inclusion of one or more ingredients that transition out of a lameller gel phase over a temperature range between about 30° C. and about 37° C. Cetostearyl alcohol is one such substance that is used with preference herein.

Desirably also, the composition is effective, when applied to the external surface of skin, to cause penetration of the one or more spinosyns to the stratum corneum layer (where mites locate), while nonetheless resulting in no or essentially no systemic absorption of the spinosyn(s) as would be evidenced by the development of concentrations of the spinosyn(s) in the circulating blood of the human or animal patient after applying the composition to the skin. As is known, adult male and breeding female mites commonly locate on the external surface of the skin while female mites do burrow and locate to the stratum corneum layer to lay eggs.

The compositions herein may be applied to the skin of the human or animal patient in any suitable manner, and left on the skin for a sufficient period for translocation of the spinosyn(s) to the stratum corneum layer and/or to treat or prevent an infection or infestation of the skin with the mites and/or for an effective time. In typical embodiments, the compositions will be applied to the skin and allowed to remain for at least about 1 hour, more preferably at least about 2 hours, and typically in the range of about 1 to about 12 hours. It will be understood, however, that longer or shorter application times may be used as are effective in controlling the mites. When using compositions herein with advantageous viscosity-decreasing properties, when the compositions are dispensed from a container (e.g. a bottle or vial), the compositions are initially relatively thick. However, upon contacting skin and thereby being warmed, the compositions lose viscosity and become much more effective to spread over large areas of skin. In this manner, controlled application is achieved while avoiding undesired loss or spillage of the composition and nonetheless providing an effective spread of the composition over large areas of the patient, which are desirable when treating or preventing infection by mites.

Any suitable therapeutic volume or mass of the composition can be applied to the skin of the human or other patient to control an existing mite infection or prophylactically prevent a mite infection, for example by killing mites and/or rendering mite eggs nonviable. The amount of the composition applied will depend upon several factors including for example the area of skin to be covered, the concentration of spinosyns in the composition, the severity of infection, and/or other factors. In certain embodiments, 10 to about 100 mL of the spinosyn-containing composition will be applied to the skin of the patient, more preferably about 30 to about 85 mL of the spinosyn-containing composition. In these or other embodiments, the spinosyn-containing composition can optionally be constituted about 0.1% to about 10% by weight of spinosyn(s), more preferably about 0.5% to about 5% by weight of spinosyn(s), and in certain embodiments the spinosyn-containing composition is the composition of Table 1. In other aspects, the composition can be applied to the skin of the patient to provide composition-coated skin with an applied level of greater than about 0.1 μg of spinosyn(s) per $cm^2$ of the composition-coated skin, preferably in the range of about 0.1 μg to about 1 μg of spinosyn(s) per $cm^2$ of composition-coated skin, and more preferably in the range of about 0.25 μg to about 0.5 μg of spinosyn(s) per $cm^2$ of composition-coated skin. Additionally or alternatively, in preferred modes of practice, a substantial percentage of the surface area of the skin of the patient will be coated with the spinosyn-containing composition, for example about 60% or greater, about 70% greater, about 90% or greater, and in certain modes essentially the entire surface area of the skin of the patient (i.e. 98% or greater).

For the purpose of promoting a further understanding of aspects of the present invention, the following specific examples are provided. It will be understood that these examples are illustrative, and not limiting, in nature.

EXAMPLE 1

Study of Scabies Treatment

A four-week, randomized, evaluator-blinded, active controlled, parallel group study is conducted to assess the effect of the formulation containing spinosyns on the treatment of scabies against placebo. The primary objective of the study is to assess the effect of the formulation containing spinosyns on scabies infestation in otherwise healthy subjects by assessing the reduction in lesions from day 1 to day 28. A group of primary subjects is enrolled in the study. All household members of subjects in the study must agree to be screened and if found to be infected agree to enroll. Family contacts are treated with a current commercial scabies treatment (e.g. active control) or invited to participate in the study if they have confirmed infestation (secondary subjects). This is a two-arm study. Subjects are randomly assigned 1:1 to placebo or to the formulation with spinosyns.

Inclusion Criteria

For inclusion criteria, subjects who have provided written informed consent and an authorization for disclosure of protected health information must meet all the following criteria.

1. Male or female, from a lower age limit to 70 years, inclusive
2. Active scabies infestation confirmed by physical and microscopic examination:
   - evidence of burrows,
   - presence of scabies lesions,
   - positive microscopic examination,
   - pruritus
3. Good general health based on medical history, clinical assessments, and laboratory assessments
4. Normal-appearing skin in noninfested areas
5. No history of chronic or recurrent dermatologic disease
6. Willingness to comply with the test procedures Exclusion Criteria For exclusion criteria, subjects are excluded if any of the following conditions exist:

1. Presence of crusted scabies
2. Allergies or sensitivities to ingredients in the test products.
3. Current pregnancy (as assessed by urine pregnancy test) or currently nursing.
4. Known renal or hepatic impairment
5. Treatment with scabicide or topical/systemic steroids within the prior 4 weeks
6. Immunodeficiency as reported in Medical History
7. Signs of systemic infection
8. Administration of systemic therapy for infectious disease within the prior 2 weeks
9. Receipt of any investigational product within the prior 4 weeks.
10. Any other conditions which, at the investigator's discretion, may interfere with the study conduct.
11. Does not have a known household affiliation with their household members, ie. does not stay in one household consistently, sleeps at one place several nights and then another Dosage Form and Route of Administration The composition of Table 1 above, or placebo, is applied in a single application (Day 1) topically to the entire body below the hairline. It is expected that about 85 mL to about 120 mL of the Table 1 composition or placebo will applied to the body of a subject depending somewhat upon the size of the subject (an estimated amount of about 6.4 μL of the composition per $cm^2$ of body surface area will be applied).

Evaluations

Assessments include evaluation of lesions/burrows, pruritus (modified pruritus score scale) and microscopy. Subjects are evaluated at baseline (Day 1) and at 2 and 4 weeks. Primary endpoint is number of lesions at Day 28.

Safety Assessments

Safety assessments will include adverse events (AEs) throughout the study period. Dermatological safety assessments (erythema, edema, rash, burning/stinging, pain, numbness, skin temperature, tingling) are made at each visit. Laboratory analyses (serum chemistry, hematology, urinalysis) are assessed at baseline (screening) and at the end of the test period.

Statistical Analysis

The changes from baseline to each time-point are calculated for each parameter by treatment group, and comparisons of the changes made between the investigational product (composition of Table 1) and the active control.

EXAMPLE 2

Skin Penetration Study

The composition of Table 1 above was used in a standard skin penetration study. A known amount of $^{14}C$-radiolabeled spinosyn mixture was added to the composition for assays, as known for such studies. The composition was applied to human cadaver skin (harvested from anterior thigh skin (used in cells 4-6) and abdominal skin (used in cells 1-3 and 7-9)) mounted in a flow-through diffusion cell system. The physiological receptor fluid was supplemented with 4% bovine serum albumin to encourage uptake of lipophilic materials. Collected samples were assayed for spinosyns A and D that were $^{14}C$-labelled. Table 2 summarizes the percentage of applied spinosyns that were absorbed into the skin after a continuous 24-hour exposure to the composition. The results showed that there appears to be absorption of spinosyns of the composition into the stratum corneum of the skin sample. However, there appeared to be very little uptake of the composition into the receptor fluid throughout the entire 24-hour fraction collection period.

Total recovery of the spinosyns relative to the mean total activity control (mass balance) in each of the diffusion cells varied from 87.7% to 108.1% of total activity control (mean=97.1%, 1 s.d.=5.6%). Based upon the absorption and penetration of the 14C-labeled spinosyns, the amounts of total spinosyns absorbed can be estimated per unit surface area of skin. Since the surface area of the exposed skin within the diffusion cells was 0.64 $cm^2$ and the dose rate for total spinosyns (both $^{14}C$-labeled and unlabeled) was 0.4 mg spinosyns/0.64 $cm^2$ tissue, the total spinosyns absorbed per $cm^2$ of skin was estimated and presented in Table 2.

TABLE 2

Amount of Spinosyns Absorbed in vitro - Leave-on Modeling

| | Amount of spinosyns absorbed | | |
|---|---|---|---|
| Diffusion Cell No. | Total Absorption (% of Applied Dose) | mg spinosyns/ .64 $cm^2$ tissue | mg spinosyns/ $cm^2$ tissue |
| 1 | 16.28% | 0.0651 | 0.1017 |
| 2 | 13.45% | 0.0538 | 0.0841 |
| 3 | 27.54% | 0.1101 | 0.1721 |
| 4 | 8.65% | 0.0346 | 0.0540 |
| 5 | 18.15% | 0.0726 | 0.1135 |
| 6 | 20.66% | 0.0826 | 0.1291 |
| 7 | 15.84% | 0.0633 | 0.0990 |
| 8 | 9.98% | 0.0399 | 0.0624 |
| 9 | 13.83% | 0.0553 | 0.0864 |
| mean | 16.04% | 0.0642 | 0.1003 |
| std.dev. | 5.71% | 0.0228 | 0.0357 |

EXAMPLE 3

Randomized, Double-Blind, Placebo-Controlled Study to Assess the Effect of the Composition of Table 1 on the Treatment of Scabies A randomized, double-blind, placebo-controlled study was conducted to assess the effect of the composition of Table 1 on the treatment of scabies in human patients.

Twenty one human subjects infected with scabies were selected for inclusion in the study—15 subjects were treated with the composition of Table 1, 5 subjects were treated with placebo (the composition of Table 1 except without the spinosyns), and 1 subject did not complete the study. Each subject applied the composition of Table 1 or the placebo to themselves. A volume of 4 oz was available for the subject to cover the skin of the body from neck to toes. The bottle was weighed before and after application to determine the actual amount of composition applied.

Efficacy was measured by the number of lesions, the number of new lesions, pruritus, observation of live mites, eggs or scybala and general improvement of failure of the treatment at four weeks after a single application of the composition of Table 1 or placebo. Efficacy of the compositions was evaluated objectively and subjectively. For example, the number of skin lesions before application and after a period of time were measured.

The results of the study evidenced the efficacy of the composition of Table 1 to control the mite infection of scabies. 11 of the 15 subjects who received the composition of Table 1 were considered cured, requiring good or moderate improvement (≥50% reduction in lesions) and negative microscopy. One of the five patients who received placebo was also considered cured, which was likely attributable to self-resolution of a mild infection.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. In addition, all publications cited herein are indicative of the abilities of those of ordinary skill in the art and are hereby incorporated by reference in their entirety as if individually incorporated by reference and fully set forth.

What is claimed is:

1. A method for controlling *Sarcoptes scabiei* mites in the treatment of human scabies, comprising:

topically applying to skin of a human a composition comprising water and:

(a) a mixture of spinosyns including Spinosyn A, Spinosyn D, and at least three other spinosyns selected from the group consisting of Spinosyn B, Spinosyn C, Spinosyn E, Spinosyn F, Spinosyn G, Spinosyn H, Spinosyn J, and Spinosyn K;

(b) one or more solubulizers for the mixture of spinosyns, said one or more solubilizers including benzyl alcohol;

(c) one or more stabilizers;

(d) one or more humectants;

(e) one or more emulsifying agents; and (f) one or more surfactant agents; and allowing the composition to remain on the skin for at least one hour.

2. The method of claim 1 wherein the one or more stabilizers comprise hydroxyethyl cellulose.

3. The method of claim 1 wherein the one or more emulsifying agents comprise Ceteareth-20.

4. The method of claim 1 wherein the one or more surfactant agents comprise stearalkonium chloride.

5. The method of claim 1 wherein the composition also comprises cetearyl alcohol.

6. The method of claim 1 wherein said topically applying comprises topically applying the composition to about 90% or greater of the surface area of the skin of the human.

7. The method of claim 1 wherein said topically applying provides about 0.1 microgram to about 1 microgram of the spinosyns per $cm^2$ of the skin to which the composition is applied.

8. The method of claim 1 wherein the skin is infested with the mites.

9. The method of claim 1 wherein the composition comprises:

about 44% water;
about 20% isopropyl alcohol;
about 10% benzyl alcohol;
about 6% hexylene glycol;
about 4.2% stearalkonium chloride;
about 3% cetearyl alcohol;
about 3% propylene glycol;
about 1.1% hydroxyethyl cellulose;
about 1% of said mixture of spinosyns;
about 0.9% ceteareth-20; and
about 0.1% butylated hydroxytoluene.

10. The method of claim 1, wherein the composition exhibits a decrease in viscosity of at least about 1000 cP when warmed from 20° C. to about 37° C. and wherein the composition has a viscosity greater than 2000 cP at 20° C. and a viscosity less than 1000 cP at 37° C.

11. The method of claim 10, wherein said allowing comprises allowing the composition to remain on the skin for at least two hours.

12. The method of claim 10, wherein the composition exhibits a nonlinear decrease in viscosity over at least one temperature range between 30° C. and 37° C.

13. A method for controlling *Sarcoptes scabiei* mites that cause human scabies comprising topically applying to skin of a human in need of control of mites that that cause human scabies a composition comprising an effective amount of one or more spinosyns, wherein the composition exhibits a decrease in viscosity of at least about 1000 cP when warmed from 20° C. to about 37° C.

14. The method of claim 13, wherein the composition has a viscosity greater than 2000 cP at 20° C. and a viscosity less than 1000 cP at 37° C., and wherein the composition exhibits a nonlinear decrease in viscosity over at least one temperature range between 30° C. and 37° C.

15. The method of claim 13, also comprising allowing the composition to remain on the skin for at least two hours.

16. The method of claim 13, wherein said one or more spinosyns is a spinosyn mixture constituted of Spinosyn A, Spinosyn D, and other spinosyns, wherein the spinosyn mixture is constituted 12% to 20% by weight of Spinosyn D and 2 to 15% by weight of the other spinosysns, with the remainder of the spinosyn mixture being constituted by Spinosyn A, and wherein the other spinosyns include at least three spinosyns selected from the group consisting of Spinosyn B, Spinosyn C, Spinosyn E, Spinosyn F, Spinosyn G, Spinosyn H, Spinosyn J, and Spinosyn K.

17. The method of claim 16, wherein said composition also comprises, water, isopropyl alcohol, benzyl alcohol, hexylene glycol, stearalkonium chloride, cetearyl alcohol, propylene glycol, hydroxyethyl cellulose, ceteareth-20, and butylated hydroxytoluene.

18. The method of claim 17, wherein said composition comprises:

about 44% water;
about 20% isopropyl alcohol;
about 10% benzyl alcohol;
about 6% hexylene glycol;
about 4.2% stearalkonium chloride;
about 3% cetearyl alcohol;
about 3% propylene glycol;
about 1.1% hydroxyethyl cellulose;
about 1% of said mixture of spinosyns;
about 0.9% ceteareth-20; and
about 0.1% butylated hydroxytoluene.

19. A method for controlling *Sarcoptes scabiei* mites that cause human scabies, comprising topically applying to skin of a human in need of control of *Sarcoptes scabiei* mites that cause human scabies, a composition comprising an effective amount of one or more spinosyns and allowing the composition to remain on the skin for at least one hour, wherein the composition is effective to cause penetration of the one or more spinosyns to the stratum corneum of skin of the human when applied externally to the skin.

20. The method of claim 19 wherein the composition also comprises:

one or more solubulizers;

one or more stabilizers;

one or more humectants;

one or more emulsifying agents; and one or more surfactant agents.

21. The method of claim 20 wherein the solubilizer comprises benzyl alcohol.

22. The method of claim 20 wherein the one or more humectants comprise propylene glycol.

23. The method of claim 20 wherein the one or more stabilizers comprise hydroxyethyl cellulose.

24. The method of claim 20 wherein the one or more emulsifying agents comprise Ceteareth-20.

25. The method of claim 20 wherein the one or more surfactant agents comprise stearalkonium chloride.

26. The method of claim 20 wherein the composition also comprises cetearyl alcohol.

27. The method of claim 20 wherein said topically applying provides about 0.1 microgram to about 1 microgram of the one or more spinosyns per $cm^2$ of the skin to which to the composition is applied, and wherein said allowing comprises allowing the composition to remain on the skin for at least two hours.

28. A method according to claim 1, wherein the composition is effective to cause penetration of the one or more spinosyns to the stratum corneum of skin of the human when applied externally to the skin.

29. The method according to claim 28, wherein the composition, when applied externally to the skin of the human, does not result in the presence of the one or more spinosyns in the systemic bloodstream of the human.

30. A method for controlling mites that burrow into and lay eggs under the surface of human skin, comprising:

(1) topically applying to skin of a human a composition comprising:

(a) a mixture of spinosyns including Spinosyn A and Spinosyn D;

(b) one or more solubulizers for the mixture of spinosyns, said one or more solubilizers including benzyl alcohol;

(c) one or more stabilizers;

(d) one or more humectants;

(e) one or more emulsifying agents; and (f) one or more surfactant agents;

wherein the composition further (i) exhibits a decrease in viscosity of at least about 1000 cP when warmed from 20° C. to about 37° C. and (ii) is effective when topically applied to human skin to cause penetration of the Spinosyn A and Spinosyn D to a stratum corneum layer of the human skin; and (2) allowing the composition to remain on the skin for at least one hour.

* * * * *